United States Patent
Fairchild et al.

(10) Patent No.: US 9,933,399 B2
(45) Date of Patent: Apr. 3, 2018

(54) SEPARATION EFFICIENCY IN SUPERCRITICAL FLUID CHROMATOGRAPHY

(71) Applicant: Waters Technologies Corporation, Milford, MA (US)

(72) Inventors: Jacob Nathan Fairchild, Upton, MA (US); Kevin Daniel Wyndham, Upton, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 257 days.

(21) Appl. No.: 14/423,949

(22) PCT Filed: Aug. 30, 2013

(86) PCT No.: PCT/US2013/057507
§ 371 (c)(1),
(2) Date: Feb. 25, 2015

(87) PCT Pub. No.: WO2014/036392
PCT Pub. Date: Mar. 6, 2014

(65) Prior Publication Data
US 2015/0212056 A1    Jul. 30, 2015

Related U.S. Application Data

(60) Provisional application No. 61/695,838, filed on Aug. 31, 2012.

(51) Int. Cl.
*G01N 30/80* (2006.01)
*B01D 15/40* (2006.01)
(Continued)

(52) U.S. Cl.
CPC .......... *G01N 30/80* (2013.01); *B01D 15/161* (2013.01); *B01D 15/1871* (2013.01);
(Continued)

(58) Field of Classification Search
None
See application file for complete search history.

(56) References Cited

U.S. PATENT DOCUMENTS

| 5,135,549 A * | 8/1992 | Phillips .................. G01N 30/30 210/198.2 |
| 2001/0013494 A1* | 8/2001 | Maiefski ................ B01D 15/08 210/656 |

(Continued)

FOREIGN PATENT DOCUMENTS

| WO | 1995003106 A1 | 2/1995 |
| WO | 2011085359 A1 | 7/2011 |
| WO | 2012058515 A2 | 5/2012 |

OTHER PUBLICATIONS

Berger, Terry A. Separation of polar solutes by packed column supercritical fluid chromatography. Journal of Chromatography A; vol. 785, Issues 1-2, Oct. 17, 1997, pp. 3-33. https://doi.org/10.1016/S0021-9673(97)00849-2.*

(Continued)

*Primary Examiner* — Paul West
*Assistant Examiner* — Mark A Shabman
(74) *Attorney, Agent, or Firm* — Womble Bond Dickinson (US) LLP; Deborah M. Vernon; Heath T. Misley

(57) ABSTRACT

The present technology uses one or more separating segments, i.e. chromatography columns, aligned in series along a flow path. The separating segments are divided by a plurality of heating elements or are heated directly. The heating elements heat the supercritical mobile phase and sample to replace heat lost due to axial expansion of the mobile phase along the mobile phase flow path.

19 Claims, 11 Drawing Sheets

(51) Int. Cl.
  *B01D 15/16* (2006.01)
  *B01D 15/18* (2006.01)
  *G01N 30/30* (2006.01)
  *G01N 30/46* (2006.01)
  *G01N 1/22* (2006.01)
  G01N 30/60 (2006.01)
  G01N 30/02 (2006.01)

(52) U.S. Cl.
  CPC ........... *B01D 15/40* (2013.01); *G01N 1/2202* (2013.01); *G01N 30/30* (2013.01); *G01N 30/465* (2013.01); *G01N 30/6039* (2013.01); *G01N 2030/025* (2013.01)

(56) References Cited

U.S. PATENT DOCUMENTS

| | | |
|---|---|---|
| 2003/0181737 A1 | 9/2003 | Nair |
| 2006/0054544 A1* | 3/2006 | Roenneburg ......... B01D 15/247 210/198.2 |
| 2006/0054558 A1 | 3/2006 | Jones et al. |
| 2009/0158820 A1* | 6/2009 | Bostrom ................ E21B 49/08 73/61.53 |
| 2009/0211978 A1* | 8/2009 | Ognibene .............. B01D 15/12 210/656 |
| 2012/0011921 A1* | 1/2012 | Broeckhoven ....... B01D 15/161 73/61.53 |
| 2014/0217031 A1* | 8/2014 | Wang .................... B01D 15/24 210/656 |
| 2015/0135861 A1* | 5/2015 | Cook .................... G01N 30/30 73/863.12 |

OTHER PUBLICATIONS

Effects of Pressure Drop, particle size and thermal conditions on retention and efficiency in supercritical fluid chromatography, Donald P. Poe, et al., Journal of Chromatography A 1216 (2009) 7915-7926.

* cited by examiner

SEPARATION EFFICIENCY IN SUPERCRITICAL FLUID CHROMATOGRAPHY

RELATED APPLICATIONS

This Application is a 35 U.S.C. § 371 national stage filing of International Application No. PCT/US2013/057507, filed Aug. 30, 2013, which claims benefit of and priority to U.S. Provisional Patent Application 61/695,838, filed on Aug. 31, 2012. The contents of the above applications are hereby incorporated by reference in their entirety.

TECHNICAL FIELD

The present disclosure relates to methods and related apparatus that lead to improvement in the separation efficiency in carbon dioxide ($CO_2$)-based chromatography and/or supercritical fluid chromatography (SFC), and in particular to methods to heat the mobile phase during a separation for improved efficiency.

BACKGROUND

Chromatographic techniques are important tools for the identification and separation of complex samples. The basic principle underlying chromatographic techniques is the separation of a mixture into individual components by transporting the mixture in a moving fluid through a retentive media. The moving fluid is typically referred to as the mobile phase and the retentive media is typically referred to as the stationary phase. The separation of the various constituents of the mixture is based on differential partitioning between the mobile and stationary phases, and subtle differences in a component's partition coefficient resulting in differential retention on the stationary phase, thus changing the separation.

There are a number of different types of chromatographic techniques, each having different operating conditions and providing different advantages for separating and analyzing samples. For example, some known techniques include liquid chromatography (LC), high-performance liquid chromatography (HPLC), ultra-high performance liquid chromatography UHPLC), gas chromatography (GC), and supercritical fluid chromatography (SFC). One difference between these techniques is the type of mobile phase material used. For example, LC and HPLC use liquids, whereas GC uses a gas as the mobile phase. SFC uses a supercritical fluid as the mobile phase for sample separation.

The supercritical fluid (SF) phase of matter is defined by the supercritical point, that is, the temperature and pressure values at which liquid and vapor have the same density and the fluid cannot be liquefied by increasing the pressure. The unique physical properties of supercritical fluids make them attractive mobile phase fluids for use in supercritical fluid chromatography (SFC). For example, supercritical fluids (or near supercritical fluids) offer the ability to dissolve samples readily like a liquid (e.g. in high-performance liquid chromatography, "HPLC"), and carry them through a stationary phase like a gas (e.g. in gas chromatography, "GC").

Another important property of SFs is that SFs provide high resolution chromatography at much lower temperatures than those used for GC, thereby enabling analysis of proteins and other biopolymers that can be sensitive to heat. For example, an analyte dissolved in supercritical $CO_2$ can be recovered by reducing the pressure and allowing the sample to evaporate under ambient laboratory conditions.

Because SFC typically uses $CO_2$ as a primary component of the mobile phase (e.g. $CO_2$ is about 100% of the mobile phase, $CO_2$ is about 99% of the mobile phase, $CO_2$ is about 97% of the mobile phase, $CO_2$ is about 95% of the mobile phase, $CO_2$ is about 90% of the mobile phase, $CO_2$ is about 80% of the mobile phase, etc.), SFC separations are inexpensive, innocuous, eco-friendly, and non-toxic. There is typically no need for the use of volatile solvent(s) (e.g., hexane). Finally, SFs, such as $CO_2$, have higher diffusion constants and lower viscosities relative to liquid solvents.

Supercritical fluids are considered compressible fluids. Unlike incompressible fluids such as liquids used for HPLC (e.g. water, methanol, hexanes, etc.) which instantly or nearly instantly equilibrate pressure evenly throughout the system when the local pressure changes at one point, compressible fluids such as supercritical fluids can experience temporary heterogeneity overall in response to a local pressure change. In the context of SFC, this means that as the supercritical fluid (or a near supercritical fluid) moves down the length of a chromatography column or separating segment, it expands. Correspondingly, as the supercritical mobile phase expands, it also cools. This phenomenon has been elucidated by A. Tarafder, G. Guiochon, *J. Chromatogr. A*, 1218 (2011) 7189; D. P. Poe, *J. Chromatogr. A*, 785 (1997), 129; D. P. Poe, J. J. Schroden, *J. Chromatogr. A*, 1216 (2009), 7915; K. Kaczmarski, D. P. Poe, G. Guiochon, *J. Chromatogr. A*, 1217 (2010) 6578. (The foregoing publications are hereby incorporated by reference in their entirety).

In some embodiments, carbon dioxide ($CO_2$) is used as the mobile phase or as a primary component of the mobile phase (i.e., $CO_2$-based chromatography). In some embodiments, chromatography using $CO_2$ as the mobile phase can be carried out at, near or below the supercritical point (e.g. as a liquid or a gas). When pumped as a liquid or a gas, $CO_2$ has a variable density due to temperature and pressure changes; that is, the density of $CO_2$ in the liquid or gas phase can vary dramatically as compared to other LC or HPLC mobile phases such as water, acetonitrile, methanol, or hexanes over small temperature or pressure changes. In general, $CO_2$ when used as a mobile phase in chromatography is considered to be a compressible fluid.

The cooling of the supercritical mobile phase or carbon dioxide mobile phase as it passes through a chromatography column (e.g. separating segment) leads to consequences for the resulting separation. One issue is that the cooling can be enough to lead to a change in state of the mobile phase. For instance, excessive cooling might cause a supercritical or near supercritical fluid to lose its supercritical or near supercritical properties and become a liquid. This would negate many of the advantages of SFC highlighted above. For example, a change of state such as becoming a liquid might increase the mobile phase viscosity and decrease the diffusion coefficients. This can lead to lower efficiency separations and higher column pressure drops. Another difficulty is that as the mobile phase cools locally, it becomes heterogeneous. For example, in addition to experiencing a temperature gradient, the mobile phase can demonstrate different physical properties such as density and viscosity along the length and radius of the separating column. Such heterogeneity of the mobile phase leads to distorted peak shape, as well as less efficient separations. These and other considerations make SFC and/or $CO_2$-based chromatography less effective due to unplanned changes of state or changes in density, especially from the impact of cooling.

SUMMARY OF THE TECHNOLOGY

The present technology is directed to methods and devices for improving the separation efficiency in $CO_2$-based chromatography and/or supercritical fluid chromatography. In particular, it is directed to methods to effectively heat the mobile phase during the separation of the sample to ensure a more homogenous mobile phase.

Instead of using one continuous chromatography column, or separating segment, to achieve separation of the sample, the present technology employs in some embodiments a plurality of noncontiguous separating segments. Between the individual separating segments is disposed a heating segment. The heating segment heats the mobile phase to replace any heat lost as a result of axial expansion of the mobile phase along the length of the separating segment. The individual separating segments (i.e. chromatography columns) in the present technology can be shorter than or equivalent to the columns used in traditional SFC and/or $CO_2$-based chromatography. In some embodiments, the separating segments are identical in size and shape to conventional separating segments, e.g. chromatography columns. However, because multiple columns are used in the present technology, the total length of column separation can in some embodiments be greater than or equal to that commonly seen in traditional SFC or $CO_2$-based chromatography setups. The length, number, and ratio of the separating segments (e.g. columns) and heating segments can be optimized to provide the best separation conditions for a given sample.

The types of separating segments can be selected in accordance with the parameters desired. For example, in some embodiments, each of the separating segments can be substantially identical in terms of length, internal diameter, shape, and stationary phase. Alternatively, in some embodiments, each individual separating segment can be selected for its unique properties. For instance, in some embodiments a flow path might be defined by different separating segments that vary in terms of length, internal diameter, and shape. In some embodiments, one or more of the separating segments can be tapered while other separating segments are not tapered. Likewise, in some embodiments, one or more of the separating segments can have an internal diameter that is larger or smaller than the internal diameter of other separating segments.

In some embodiments, the stationary phase in the separating segments can differ. That is, a first separating segment can contain a first stationary phase which differs from a second stationary phase contained within a second separating segment included along a flow path that includes the first separating segment. In some embodiments, the first and second stationary phases are substantially identical.

In an alternative embodiment, instead of using multiple separating segments divided by one or more heating segments, a single separating segment can be used. In such embodiments, the single separating segment is heated axially and in a specific direction. That is, the heat is applied axially in an outlet-to-inlet direction. This specific type of heating, i.e. heating axially in an outlet-to-inlet direction, can also be applied to multiple, separate contiguous separating segments.

In an aspect, the present technology features a method for separating a sample in a compressible fluid chromatography device. The device defines a flow path and comprises a plurality of segments for separating the sample, as well as a plurality of segments for heating at least a portion of the flow path. The method includes introducing the sample into the compressible fluid chromatography device and separating the sample along at least two non-contiguous segments of the compressible fluid chromatography device along the flow path. The non-contiguous segments used for separating the sample are themselves separated by at least one heating segment, that is, the non-contiguous segments are linearly separated, i.e. not directly adjacent along a flow path. The method further includes heating one or more of the plurality of segments of the compressible fluid chromatography device to reduce expansion of the compressible fluid along the flow path.

In one or more embodiments, the method further includes collecting fractions of the sample after separation. In some embodiments, multiple different types of separating segments are used. In some embodiments, the separating segments used are of the same type. In some embodiments, the method further includes pre-heating the sample before separation with a pre-heater. In embodiments, the pre-heater is an oven, such as, for example a traditional oven, a vacuum-chamber oven, an adiabatic oven, a near-adiabatic oven, a convective flow oven, or an isothermal oven. In some embodiments, the heater can employ an oscillating magnetic field. For example, microwave or IR heaters can be used. For example, the heater can be a magnetic frit material inside a column (e.g. separating segment). An oscillating magnetic field could be used to heat the magnetic frit material. Additionally, in some embodiments, an entire SFC system can be patterned onto a chip, and the heater can be part of the same chip, or part of a different SFC chip. Additionally, each heater can be of the same type, or some heaters can be of a different type. For example, some heaters can use differentiated heating, while other heaters can use feedback heating, and still others can use static heating.

In some embodiments, the heating segment is any of the pre-heaters described above. In some embodiments, the heater is a flow through heater. In other embodiments, the heating segment is a clip-on heater. In embodiments, the heating segment is a microfluidic heater. In one or more embodiments, the heating segment is made of titanium, steel, gold, ceramic, a polymer, or combinations thereof.

In one or more embodiments of the above method, the heating volume is minimized in accord with the heat flux generated. In some embodiments, the heating volume is about 0.001-10 mL. In some embodiments, the heating segment length is minimized in accord with the heat flux generated. In embodiments, the heating segment length is about 0.1-40 mm.

In some embodiments, the plurality of segments comprises two or more separating segments. In one or more embodiments, the number of separating segments is between 2 and 5. In some embodiments, the number of separating segments is between 2 and 4. In embodiments, the number of separating segments is between 2 and 3.

In one or more embodiments, the number of heating segments is between 1 and 5. In some embodiments, the number of heating segments is between 1 and 4. In one or more embodiments, the number of heating segments is between 2 and 3. In some embodiments, the number of heating segments is 2. In other embodiments, the number of heating segments per separating segment is 2. In some embodiments, the number of heating segments per separating segment is 1.

In one or more embodiments of the technology, the segments (e.g. the heating and separating segments) of the compressible fluid chromatography device are connected by interconnecting tubing. In embodiments, the internal diameter of the interconnecting tubing is about 2.5-2500 μm. In one or more embodiments, the internal diameter of the interconnecting tubing is about 10-500 μm. In embodiments, the internal diameter of the interconnecting tubing is about 50-350 µm. In some embodiments, the internal diameter of the interconnecting tubing is about 80-200 µm.

In embodiments of the technology, the length of the interconnecting tubing is minimized in accord with the heat flux generated. In some embodiments, the length of the interconnecting tubing is about 0.1-40 mm. In embodiments, the heat flux is optimized in accord with the fluid or fluid mixture of use. In one or more embodiments, the heat flux is about 0.001-100 J/mol K. In some embodiments, the heat flux is about 20-80 J/mol K.

In some embodiments, the initial temperature range for a column (e.g. separating segment) is about 273-573 K. In one or more embodiments, the initial temperature is about 283-473 K. In some embodiments, the initial temperature is about 293-373 K. In other embodiments, the initial temperature is about 308-328 K. The temperature of the heating segment can be higher or equal to the temperature of the column (e.g. separating segment).

In one or more embodiments, the method further includes detecting a portion of the sample. In some embodiments, the compressible fluid is supercritical or near supercritical carbon dioxide. In some embodiments, the compressible fluid is a chlorofluorocarbon (e.g. Freon), $N_2O$, or $SF_6$, all of which may be at or near the supercritical point.

In another aspect, the present invention features a method for separating a sample in a carbon dioxide-based chromatography device defining a flow path. The method includes providing a carbon dioxide-based chromatography device including a plurality of segments for separating the sample and/or heating at least a portion of the flow path. The method further includes introducing the sample into the chromatography device in which carbon dioxide is used as a mobile phase. The method further includes separating the sample along two non-contiguous segments of the flow path of the mobile phase through the device. The method further includes heating at least one of the plurality of segments disposed between the two non-contiguous segments of the flow path of the carbon dioxide-based chromatography device to reduce expansion of the carbon dioxide along the fluid path.

In one or more embodiments, the method further includes collecting fractions of the sample after separation. In some embodiments, multiple different types of separating segments are used (e.g. separation segments can differ in size and/or shape and/or stationary phase). In some embodiments, the separating segments used are of the same type. In some embodiments, the method further includes pre-heating the sample before separation with a pre-heater. The pre-heater can be, but is not limited to, any of the pre-heating devices described above.

In some embodiments, the heating segment can be any of those described above. In one or more embodiments of the above aspect, the heating volume is minimized in accord with the heat flux generated. In some embodiments, the heating volume is about 0.001-10 mL. In some embodiments, the heating segment length is minimized in accord with the heat flux generated. In some embodiments, the heating segment length is about 0.1-40 mm.

In some embodiments, the segments of the carbon dioxide-based chromatography device are connected by interconnecting tubing. In some embodiments, the internal diameter of the interconnecting tubing is about 2.5-2500 µm. In some embodiments, the internal diameter of the interconnecting tubing is about 10-500 µm. In some embodiments, the internal diameter of the interconnecting tubing is about 50-350 µm. In some embodiments, the internal diameter of the interconnecting tubing is about 80-200 µm. In some embodiments, the length of the interconnecting tubing is minimized in accord with the heat flux generated. In some embodiments, the length of the interconnecting tubing is about 0.1-40 mm.

In one or more embodiments, the heat flux is optimized in accord with the fluid of fluid mixture of use. In one or more embodiments, the heat flux is about 0.001-100 J/mol*K. In one or more embodiments, the heat flux is about 20-80 J/mol*K.

In one or more embodiments, the plurality of segments comprises two or more separating segments. In one or more embodiments, the number of separating segments is between 2 and 5. In one or more embodiments, the number of separating segments is between 2 and 4. In one or more embodiments, the number of separating segments is between 2 and 3. In one or more embodiments, the number of heating segments is between 1 and 5. In one or more embodiments, the number of heating segments is between 1 and 4. In one or more embodiments, the number of heating segments is between 2 and 3. In some embodiments, the number of heating segments is 2. In some embodiments, the number of heating segments per separating segment is 2. In one or more embodiments, the number of heating segments per separating segment is 1.

In some embodiments, the initial temperature is about 273-573 K. In one or more embodiments, the initial temperature is about 283-473 K. In some embodiments, the initial temperature is about 293-373 K. In embodiments, the initial temperature is about 308-328 K.

In one or more embodiments, the method further comprises detecting a portion of the sample. In some embodiments, the carbon dioxide at or near supercritical conditions within at least a portion of the at least two non-contiguous segments during separation of the sample.

In another aspect, the present invention features a carbon dioxide-based chromatography apparatus for separating a sample. The apparatus includes an inlet tubing. The apparatus also includes a plurality of segments oriented in series defining a flow path connected to the inlet tubing. At least two non-contiguous segments along the flow path are capable of separating a sample based on a defined physical property. At least one heating segment is disposed between the non-contiguous separating segments of the apparatus. The apparatus also includes an outlet tubing connected to the plurality of segments at the opposite end of the inlet tubing.

In some embodiments, the apparatus further includes means for collecting fractions of the sample after separation. In some embodiments, the apparatus uses multiple different types of separating segments. In some embodiments, the apparatus uses the same type of separating segment. In some embodiments, the apparatus further includes a pre-heater to pre-heat the sample before separation. The pre-heater can include, but is not limited to, any of the pre-heaters described above.

In one or more embodiments of the apparatus, the heating segment is a flow through heater. In one or more embodiments of the apparatus, the heating segment is a clip-on heater. In some embodiment of the apparatus, the heating segment is a microfluidic heater. In other embodiments of the apparatus, the heating segment is made of titanium, steel, gold, ceramic, a polymer, or combinations thereof.

In some embodiments of the apparatus, the heating volume is minimized in accord with the heat flux generated. In some embodiments of the apparatus, the heating volume is about 0.001-10 mL. In embodiments of the apparatus, the heating segment length is minimized in accord with the heat flux generated. In one or more embodiments of the apparatus, the heating segment length is about 0.1-40 mm.

In embodiments of the apparatus, the number of heating segments is between 1 and 5. In embodiments of the apparatus, the number of heating segments is between 1 and 4. In embodiments of the apparatus, the number of heating segments is between 2 and 3. In embodiments of the apparatus, the number of heating segments is 2. In embodiments of the apparatus, the number of heating segments per separating segment is 2. In embodiments of the apparatus, the number of heating segments per separating segment is 1.

In one or more embodiments of the apparatus, the plurality of segments comprises two or more separating segments. In embodiments of the apparatus, the number of separating segments is between 2 and 5. In embodiments of the apparatus, the number of separating segments is between 2 and 4. In embodiments of the apparatus, the number of separating segments is between 2 and 3.

In embodiments of the apparatus, the segments (e.g. the heating and separating segments) of the carbon dioxide-based chromatography device are connected by interconnecting tubing. In some embodiments of the apparatus, the internal diameter of the interconnecting tubing is about 2.5-2500 μm. In one or more embodiments of the apparatus, the internal diameter of the interconnecting tubing is about 10-500 μm. In some embodiments of the apparatus, the internal diameter of the interconnecting tubing is about 50-350 μm. In some embodiments of the apparatus, the internal diameter of the interconnecting tubing is about 80-200 μm. In one or more embodiments of the apparatus, the length of the interconnecting tubing is minimized in accord with the heat flux generated. In some embodiments of the apparatus, the length of the interconnecting tubing is about 0.1-40 mm.

In some embodiments of the apparatus, the heat flux is optimized in accord with the fluid of fluid mixture of use. In one or more embodiments of the apparatus, the heat flux is about 0.001-100 J/mol K. In some embodiments of the apparatus, the heat flux is about 20-80 J/mol K.

In some embodiments of the apparatus, the initial temperature is about 273-573 K. In embodiments of the apparatus, the initial temperature is about 283-473 K. In embodiments of the apparatus, the initial temperature is about 293-373 K. In embodiments of the apparatus, the initial temperature is about 308-328 K.

In one or more embodiments, the apparatus further comprises means for detecting a portion of the sample. In embodiments of the apparatus, the carbon dioxide is at or near supercritical conditions within at least a portion of the at least two non-contiguous segments during separation of the sample.

In yet another aspect, the present invention features a method for separating a sample in a carbon dioxide-based chromatography device. The method includes providing a carbon dioxide ($CO_2$)-based chromatography device defining a mobile phase flow path wherein the device has an inlet, a contiguous separating segment and an outlet all in fluid communication, such that the outlet is downstream of the inlet and the separating segment is disposed between the inlet and the outlet along the flow path. The method further includes introducing a sample into the chromatography device via the inlet, separating the sample along the separating segment, wherein the separating segment comprises a stationary phase adapted to separate components of a sample, and heating the separating segment in an axial direction from the outlet to the inlet.

In some embodiments, the method further includes collecting fractions of the sample after separation. The method can include using multiple different types of separating segments, or the same type of separating segments. The method can include pre-heating the sample before separation with a pre-heater. In some embodiments, the heating segment has the characteristics of a pre-heater. In some embodiments, the carbon dioxide mobile phase is at or near supercritical conditions within at least a portion of the separating segment Given the above features, the advantages of the present technology are numerous. In one instance, the technology allows the use of shorter separating segments, i.e. shorter columns, than in traditional carbon dioxide-based or SFC systems. In general, shorter separating segments lead to less axial expansion of the mobile phase, thus less heat loss as a result. A second advantage is that by heating the mobile phase between the separating segments, the temperature of the mobile phase is kept more consistent than in traditional carbon dioxide-based or SFC chromatography systems. Additionally, when heating the mobile phase axially in an outlet-to-inlet direction, heat can be applied directly to the point of the separating segment where the most heat is being lost due to axial expansion in an inlet-to-outlet direction of the mobile phase. By keeping the temperature of the mobile phase consistent, other physical properties of the mobile phase, e.g. density, compressibility, etc., are also kept more consistent. Therefore the mobile phase as a whole is ultimately more homogeneous than in traditional carbon dioxide-based or SFC chromatography systems. Ensuring a homogenous mobile phase translates to a more reliable, robust process for separating a sample that is more consistent across runs and more convenient for the user.

BRIEF DESCRIPTION OF THE DRAWINGS

The features and advantages of the technology described above, taken together with further advantages, can be better understood by referring to the following description taken in conjunction with the accompanying drawings. The drawings are not necessarily to scale, emphasis instead generally being placed upon illustrating the principles of the technology.

DETAILED DESCRIPTION

Figure 1:
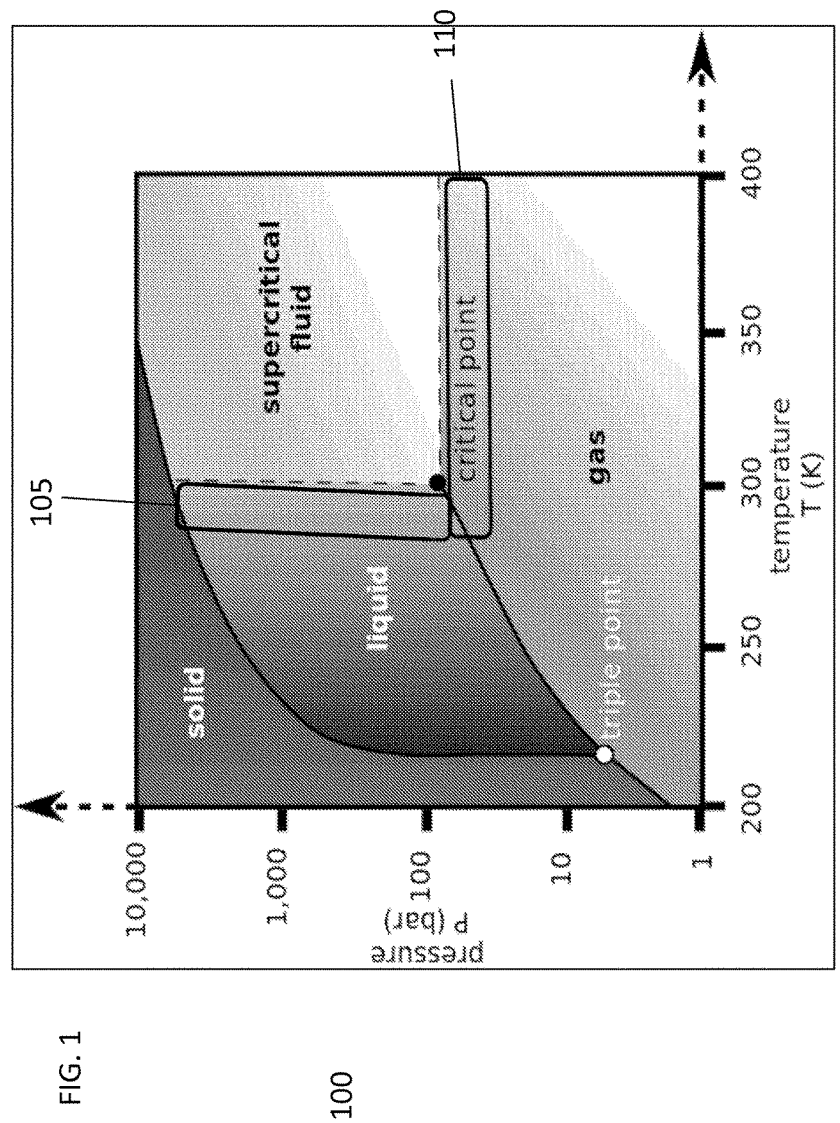
FIG. 1 shows a phase diagram for carbon dioxide ($CO_2$) with temperature denoted along the x axis and pressure denoted along the y axis.

Methods and apparatuses for effectively heating the mobile phase used in SFC, particularly SFC using carbon dioxide as a mobile phase, can greatly improve the chromatographic process. As explained by A. Tarafder & G. Guichon (*J. Chromatogr. A*, 1218, (2011) 7189, the contents of which are hereby incorporated in their entirety by reference) "[t]he thermal expansion coefficient increases markedly [near the critical point], leading to a rapid rate of temperature drop with decreasing density. The thermal diffusivity, on the other hand, decreases sharply in this zone, which reduces the ability of the fluid to reach temperature equilibrium and relax the temperature difference through heat transfer. This double effect renders highly probable the formation of a production-transmission imbalance in which the rate of heat absorption (due to eluent expansion) outweighs the rate of heat transmission, leading to a significant thermal heterogeneity throughout the column."

The thermal heterogeneity described above (e.g. the cooling of the mobile phase as it expands along the length of the chromatography column) can lead to distorted peak shapes and inefficient separations in SFC or carbon dioxide-based chromatography. The consequence of axial movement along a separating segment (i.e. chromatography column) in SFC or carbon dioxide-based chromatography is thus different than that which is commonly observed in HPLC. Indeed, because HPLC uses liquids (i.e. incompressible fluids), one challenge is the generation of heat due to friction as the mobile phase liquids encounter the stationary phase particles within the separating segment. The effect is more pronounced when using viscous solvents. In order to counteract such effects, Broeckhoven et al. describes a system for use in LC wherein the mobile phase is cooled by cooling segments disposed between noncontiguous separating segments (PCT/EP2010/054033; the teachings of this application are hereby incorporated by reference in their entirety).

The same heterogeneity issue is also present in carbon dioxide-based chromatographic systems operating far below supercritical conditions. For example, cooling experienced by a system with a carbon dioxide mobile phase with a separation temperature and pressure of below 304 K and 7.39 MPa, is still susceptible to distorted peak shape due to cooling.

Because supercritical (or near supercritical) fluid mobile phases of certain mobile phase chemicals (e.g. $CO_2$, nitrous oxide ($N_2O$), sulfur hexafluoride ($SF_6$), chlorofluorocarbons (CFCs) such as Freon, or diluted mixtures of the foregoing with a modifier) are not highly viscous, the generation of heat during separation in some embodiments is not a serious issue in SFC or other forms of compressible fluid chromatography such as carbon dioxide-based chromatography. Instead, the cooling of the mobile phase that takes place along a chromatography column (e.g. separating segment) leads to thermal and physical heterogeneity within the mobile phase. This happens because in some embodiments of SFC and other forms of compressible fluid chromatography (e.g. $CO_2$-based chromatography), a significant pressure is built upon the column (e.g. separating segment) inlet. The fluid is compressed at the inlet and a pressure gradient along the length of the separating segment is created. That pressure is released axially along a column as the mobile phase flows through the separating segment. The release of pressure causes expansion of the compressed fluid and subsequent cooling of the fluid inside the separating segment. The end results are thermal gradients inside the separating segments, which reduce the chromatographic performance (e.g. column efficiency). Also, a phase change is possible for the supercritical fluid (or near supercritical fluid) involved. Lowering the mobile phase temperature can create a sub-critical fluid resulting in a denser mobile phase. This would significantly change the chromatographic conditions and resulting separation. In addition, the density of a $CO_2$ mobile phase can fluctuate and/or vary to a degree significant enough to affect the separation and/or result.

A practitioner of ordinary skill will understand that all fluids (e.g., gases and liquids) theoretically have some finite degree of compressibility. That is, all fluids will theoretically respond with a change in volume upon application of a pressure to the fluid. However, in the case of many liquids, (e.g., water, methanol, acetonitrile, isopropyl alcohol) the degree of compressibility is negligible (as compared to degree of change in one or more of compressibility/density/viscosity/solvating power of $CO_2$) and can be ignored for the purposes of a chromatographic separation.

The term "compressible fluid" as used herein is understood to mean a fluid that is suitable for use as a mobile phase in a chromatography system that is substantially compressible. For example, a compressible fluid can be one for which compressibility is actively monitored and/or compensated for throughout each pump stroke and throughout the entire chromatographic apparatus. In some embodiments, the density of the compressible fluid changes or varies during each pump stroke if not actively compensated for throughout fluid delivery. A compressible fluid for use in chromatography is also one that is attainable for chromatographic systems. For instance, water can be considered a compressible fluid when it exists in a supercritical state. However, in water, the critical point occurs at about 647 K (374° C.; 705° F.) and 22.064 MPa (3200 PSIA or 218 atm). These conditions can often be difficult to achieve using commonly available laboratory (e.g., chromatography) equipment. Alternatively, carbon dioxide exists as a supercritical fluid above its critical temperature (304.25 K) and critical pressure (72.9 atm/7.39 MPa) and is thus considered a compressible fluid for the purposes of this application. These conditions can be much more readily achievable in a typical laboratory setup. Some exemplary compressible fluids for use in chromatography are carbon dioxide ($CO_2$), nitrous oxide ($N_2O$), chlorofluorocarbons (CFCs), nitrogen gas ($N_2$), xenon gas (Xe) and argon gas (Ar).

As used herein, the term "compressible fluid chromatography device" means a chromatography system that uses a compressible fluid as a primary component of the mobile phase. Similarly, a "carbon dioxide-based chromatography device" means a chromatography system that uses carbon dioxide as a primary component of the mobile phase.

FIG. 1 shows a phase diagram for carbon dioxide ($CO_2$) with temperature denoted along the x axis and pressure denoted along the y axis. At a certain point of temperature and pressure, known as the critical point, (i.e. 304 K and 73 bar) $CO_2$ exists no longer as a gas or liquid, but instead as a supercritical fluid. In some embodiments, fluids that are slightly below the critical point can have properties similar to supercritical fluids. Therefore, SFC can also take place using a near-supercritical fluid as a mobile phase. A near-supercritical fluid is one that exists at a point of temperature and pressure very near, but below, the critical point. These regions are shown in chart 100, and more specifically in region 105 and 110. These regions roughly define the borders for the "near supercritical" phase of matter, e.g. $CO_2$.

To ensure that the mobile phase is maintained in a supercritical phase or a near supercritical phase, a chromatography column (e.g. separating segment) can be segmented into relatively shorter segments between which the mobile phase (e.g. $CO_2$) can be heated appropriately. That is, heating the fluid path during or in between separation events is employed to improve overall separation results. In one or more embodiments, active feedback heaters could be chosen over static heaters, to optimize heating efforts.

In some embodiments, instead of using carbon dioxide as a mobile phase above the supercritical point, carbon dioxide is used as a mobile phase below the supercritical point. For instance, carbon dioxide can be used as a chromatographic mobile phase in the gas or liquid form. However, even when carbon dioxide is used as a mobile phase below its supercritical point, its density can vary throughout the course of a separation due to axial expansion and cooling. This can lead to inefficiencies over the course of a separation.

While FIG. 1 illustrates a phase diagram for $CO_2$, the same concepts would be applicable for other SFC solvents, as well as mixtures of SFC solvents (e.g. primary solvents) with modifiers (e.g. secondary solvents). For example, in some SFC embodiments, the mobile phase comprises $CO_2$ as a primary solvent (e.g. about 90% $CO_2$) and methanol as a secondary solvent (e.g. about 10% methanol).

Figure 2A:
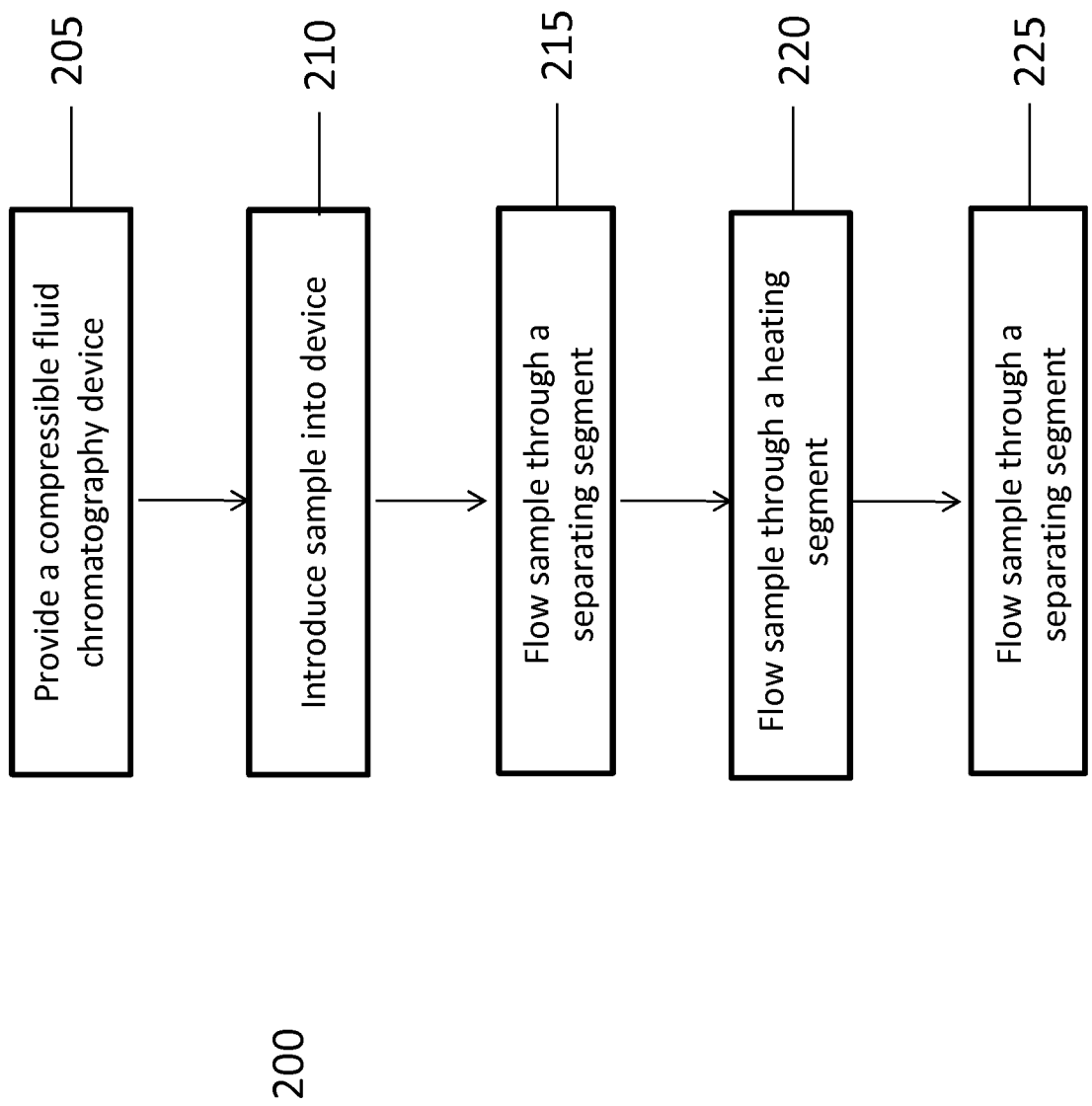
FIG. 2A shows a flow chart defining a method of the present technology.

FIG. 2A shows a flow chart detailing one embodiment of the steps of the method 200 of the present technology. In step 205, the user provides a compressible fluid chromatography device, e.g. an SFC device and/or a $CO_2$-based chromatography device. While any type of SFC system can be used in the method, exemplary devices include, but are not limited to the Method Station X5 SFC system, available from Waters Technologies Corporation, Milford, Mass., USA, and the ACQUITY $UPC^2$ system, available from Waters Technologies Corporation, Milford, Mass., USA. Step 210 shows introducing the sample into the chromatography device. Step 215 shows flowing the sample through a separating segment (e.g. short chromatography column). As pressure is released axially along the length of the separating segment, the mobile phase expands and heat is lost. Therefore, in step 220, the mobile phase is flowed through a heating segment to replace at least a portion of the heat lost due to axial expansion, and help maintain homogeneity of the mobile phase. In step 225, the mobile phase is then again flowed through a separating segment for further separation of the sample.

The heating segments, e.g. those used in step 220, can include heaters integrated into the segments, such as within the walls of the heating segments, or in some embodiments applied to an exterior wall of the heating segments, e.g. a thermal wrap or applied coating. Some non-limiting examples of heaters within the wall of the heating segment include a heater cartridge in combination with a heater block assembly made of a thermally conductive material, such as that described in international patent publication No. WO 2011/085359, hereby incorporated by reference, and heater cartridge described in US patent publication No. US 2006/0054558 hereby incorporated by reference. Non-limiting examples of heaters applied to external walls include a resistance wire wrapped around a segment, such as described in US patent publication No. US 2006/0054558, and a thermally conductive film heated from an active heating source, such as described in US publication No. 2009/0211978, hereby incorporated by reference.

Other types of heaters that can be applied to the heating segments include, for example, a traditional oven, a vacuum-chamber oven, an adiabatic oven, a near-adiabatic oven, a convective flow oven, an isothermal oven, a flow through heater, a clip-on heater, or a microfluidic heater. Additionally, magnetic field/oscillating heaters can be used, or microwave or IR heaters can be used. For example, in some embodiments a metallic frit or wall material can be heated through microwave or IR technology. In one or more embodiments, the heating segment (e.g. the walls forming the fluid path) is made of titanium, steel, gold, ceramic, a polymer, or combinations thereof. In some embodiments, the SFC device and heater can be patterned onto a chip. In some embodiments, the heater can be on the same chip, or on a different chip.

In some embodiments, the heat may be applied in a given direction. For instance, the heat may be applied in an axial direction along the length of a heating and/or separating segment. In some embodiments, the heat is applied axially in a direction from the outlet of the chromatographic system towards the inlet of the system, or in a direction from the inlet towards the outlet. In cases where heat is applied in a direction from outlet to inlet, the mobile phase can be warmed the most at points where the cooling of the mobile phase due to axial expansion is most pronounced, that is, towards the outlet of the chromatography system. In some embodiments, the heating can be applied in an axial direction from the outlet to inlet to the radial center of the outlet of the chromatography system.

Figure 2B:
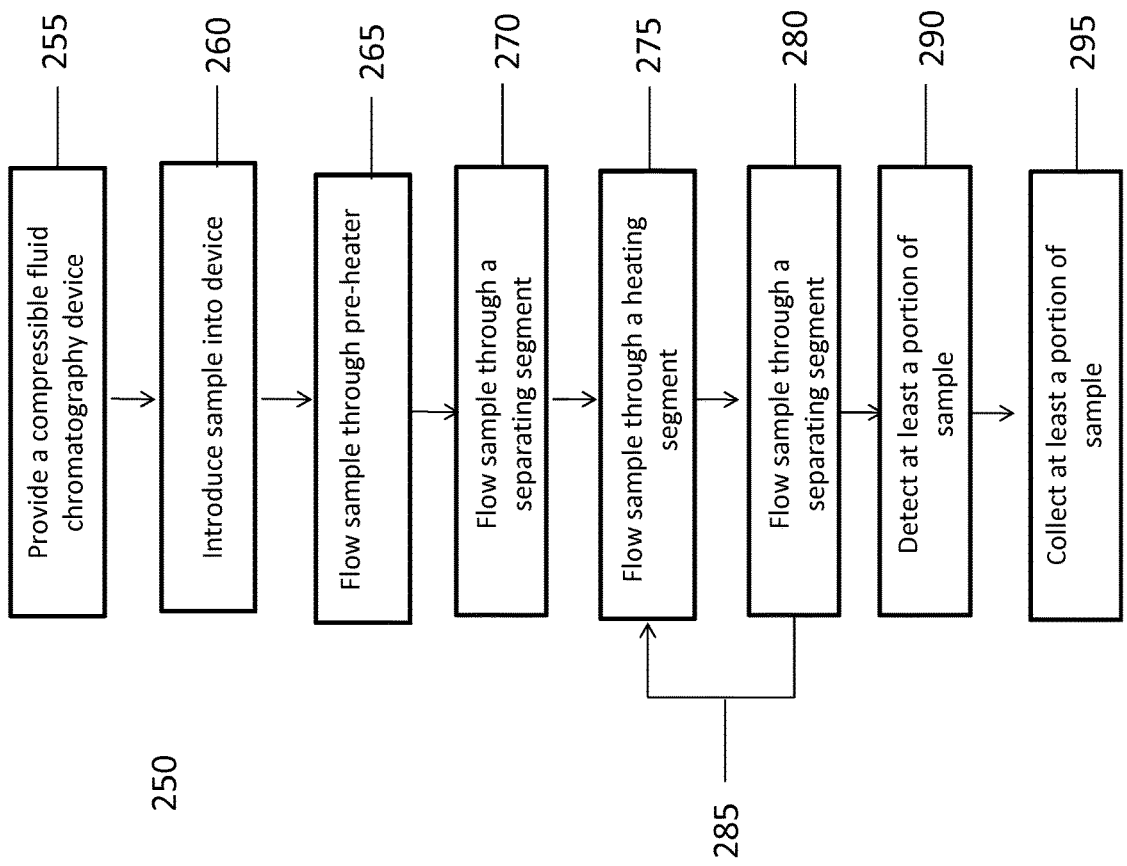
FIG. 2B shows a flow chart defining another method in accordance with the present technology, along with optional steps to enhance the utility of the present technology.

FIG. 2B shows a preferred embodiment of the steps of the method, 250 of the present technology. In step 255, the user provides a compressible fluid chromatography device, e.g. an SFC and/or carbon dioxide-based device. Step 260 shows introducing the sample into the chromatography device. Step 265 shows flowing the sample through an optional pre-heater. The pre-heater can be, but is not limited to, any of those heaters described above, i.e. it can be substantially similar to the heating segments. Step 270 shows flowing the sample through a separating segment. As pressure is released axially along the length of the separating segment, the mobile phase expands and heat is lost. Therefore, in step 275, the mobile phase is flowed through a heating segment to replace at least a portion of the heat lost due to axial expansion, and help maintain homogeneity of the mobile phase. The heater can be, but is not limited to, any of those described above. Additionally, in some embodiments the heat is applied in a specific direction such as axially from outlet to inlet. In step 280 the mobile phase is then again flowed through a separating segment for further separation of the sample. Optional step 285 shows flowing the sample once again through a heating segment to replace at least a portion of the heat lost due to expansion along the separating segment. The sample is then flowed once again through a separating segment. In some embodiments, there can be continued iterations of step 285. The number of iterations of step 285 can be optimized according to the conditions of the individual separation. Optional step 290 shows detecting at least a portion of the sample after the mobile phase has passed through the separating and heating segments. Option step 295 shows collecting at least a portion of the sample.

Figure 3:
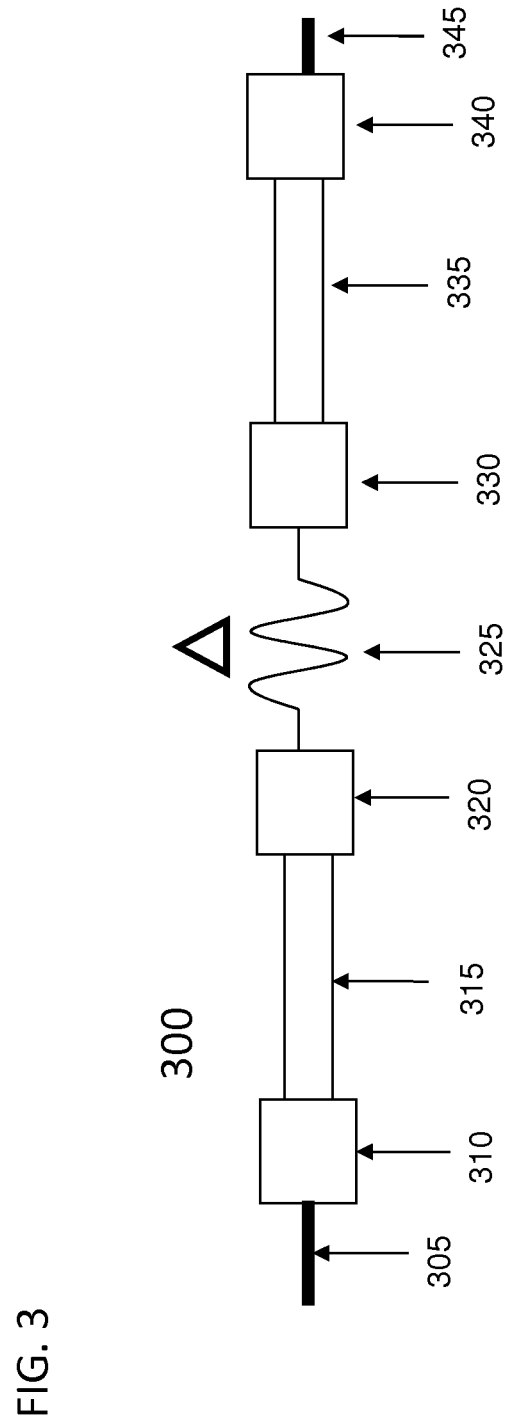
FIG. 3 shows one embodiment of the apparatus of the present technology.

FIG. 3 shows one embodiment of the apparatus 300 of the present technology. The sample and mobile phase are introduced via the inlet tubing 305. The sample stream, e.g. the sample and mobile phase, pass through a plurality of segments oriented in series along a flow path. The plurality of segments includes at least two non-contiguous separating segments (i.e. segments capable of separating a sample based on a defined physical property) and a heating segment disposed between the separating segments. Connecting the separating segments and heating segments are inlets/outlets formed of interconnecting tubing. For example, the sample stream provided through inlet tubing 305 passes through an inlet 310 and into the separating segment 315, where the analyte is at least partially separated based on a defined physical and/or chemical property. The mobile phase then passes through an outlet 320 and through a heating segment 325. The heating segment replaces at least a portion of the heat lost due to axial expansion through the separating segment. The fluid then flows into a next inlet 330, and into the next separating segment 335. The mobile phase then flows through a next outlet 340 and through the outlet tubing 345.

Within the separating segments, e.g. 315 and 335, the sample stream flows past a retentive media, and at least partially separates in accordance with chromatographic principles. During this portion of separation, the mobile phase, (e.g. $CO_2$, or $CO_2$ in combination with a modifier solvent such as methanol and/or additives) expands axially and radially along the length of the separating segment as a result of the pressure gradient that exists within the separating segment. The mobile phase loses heat as it expands, leading to axial and radial heterogeneity along the separating segment. In some embodiments, the radial heterogeneity is the primary cause of peak distortion despite the fact that cooling can come from fluid expansion in the axial direction. For instance, in some embodiments when inadequate heaters are employed, the cold mobile phase near the separating segment walls is heated easily, while the radial center remains cool, leading to peak distortion. Thus the heating segments are an important feature to replace at least a portion of the heat lost, and help ensure homogeneity of the mobile phase.

The separating segments, e.g. 315 and 335 are packed internally with a stationary phase designed to temporarily retain a portion of the sample. In some cases, the stationary phase comprises solid particles, fully porous, or superficially porous particles, or a porous monolithic structure, or combinations thereof. The porous stationary phase (i.e. packed particles, or a porous monolith, etc. creates a flow path for the mobile phase to flow through. In some embodiments, the stationary phase (e.g. packed particles or a porous monolith) is formed of silica, a hybrid inorganic/organic particle (e.g. polyethoxysilane), titania, alumina, zirconia, ceria, or other metal oxide, polymeric and combinations thereof. The particles can be spherical, or can be other shapes.

The non-contiguous separation segments, e.g. 315 and 335, are in some embodiments shorter in length than standard or conventional chromatography separating segments, i.e. columns. For example, in applications calling for a 25 mm column (i.e. separating segment), each of the non-contiguous separating segments could have a length of 15 mm or less. In one particular embodiment, including two separating segments, the length of the separating segments is 12.5 mm.

In some embodiments, the separating segments can be wrapped in an insulating material to reduce or minimize heat loss due to expansion during separation within the separating segments. For example, a separating segment can be wrapped in aluminum foil to prevent heat loss. Alternatively, separating segments can be wrapped in, for example, cotton or wool cloth.

The heating segment, e.g. 325, as described above, can include heaters integrated directly into the walls of the segment (e.g. heating cartridge), or applied to an exterior wall of the heating segment (e.g. wire or thermally conductive coating). In one or more embodiments, the heating segment is formed of titanium, steel, gold, ceramic, a polymer, or combinations thereof. The heating segment includes a heater that conductively heats the fluid flow passing through the heating segment to replace at least a portion of the energy lost in the previous separating segment 315. As further described above, the heaters of the heating segment can include a traditional oven, a vacuum-chamber oven, an adiabatic oven, a near-adiabatic oven, a convective flow oven, an isothermal oven, a flow through heater, a clip-on heater, or a microfluidic heater. Additionally, magnetic field/oscillating heaters can be used, or microwave or IR heaters can be used. For example, in some embodiments a metallic frit or wall material can be heated through microwave or IR technology.

In one or more embodiments, the heating segment 325 is designed to have a size or shape to optimize heating of the sample stream after passing through a separation segment. In some embodiments, the volume of the heating segment is minimized in accord with the heat flux generated. For example, the volume of the heating segment is between about 0.001 to 10 mL. In some embodiments, the length of the heating segment is minimized in accord with the heat flux generated. For example, the length of the heating segment is between about 0.1 to 40 mm.

In one or more embodiments, the heater of the heating segment 325 has a heat flux optimized in accordance with the fluid (e.g. $CO_2$) or fluid mixture, e.g. sample stream used in the apparatus 300. For example, in some embodiments, the heat flux of the heater utilized is about 0.001-100 J/mol K. In some embodiments, the heat flux is about 20-80 J/mol K.

Apparatus 300 includes interconnecting tubing (e.g. inlets and outlets 310, 320, 330, and 340) to fluidly connect the heating segments 325 and separating segments 315 and 335. In some embodiments, the interconnecting tubing is designed not only to fluidly connect segments 315 and 335 with 325, but also to limit the amount of dead volume in the system. Dead volume, as understood herein, is a term used in the art to refer to any portion of a chromatographic flow path that does not serve a clear function (e.g. separation of a sample). Dead volume is therefore understood to mean the volume of interconnecting tubing that does not substantially separate components of the sample or heat the mobile phase. For example, in order to minimize dead volume, the internal diameter of the interconnecting tubing can be between about 2.5 to 2500 μm, about 10 to 500 μm, 50-350 μm, 80 to 200 μm. In some embodiments, the length of the interconnecting tubing is minimized in accordance with the heat flux generated. For example, in some embodiments the length of the interconnecting tubing is 0.1 to 40 mm.

Figure 4:
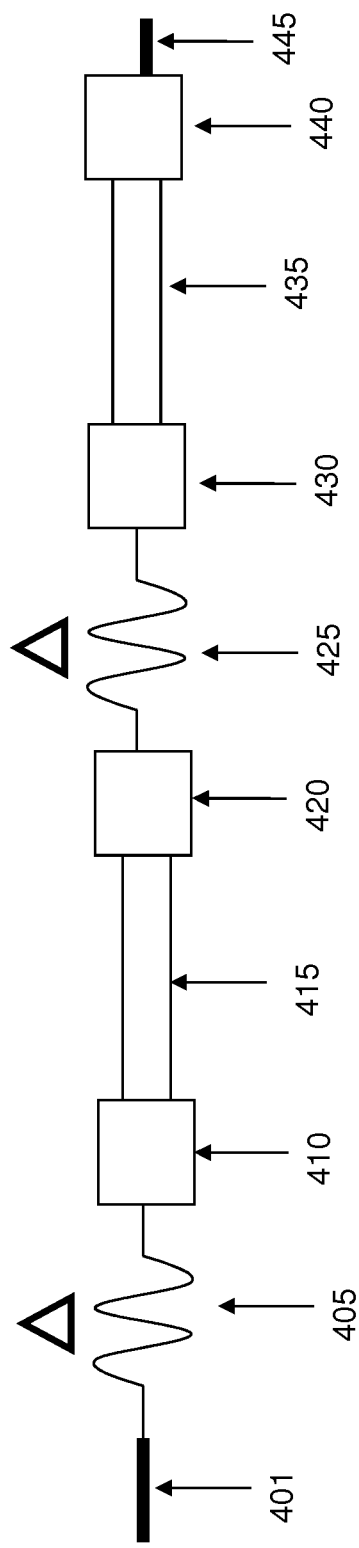
FIG. 4 shows another embodiment of the apparatus of the present technology.

FIG. 4 shows another embodiment of a segmented separation device 400 in accordance with the present technology. In this embodiment, the segmented separation device includes a pre-heater to thermally condition the sample stream prior to any separation events. The sample and mobile phase, i.e. the sample stream, are introduced via the inlet tubing 401. The mobile phase then passes through an optional pre-heater 405. The pre-heater can be, but is not limited to, any of those described above. The sample then passes through an inlet 410 and into a separating segment 415. The mobile phase then passes through an outlet 420 and through a heating segment 425. The heating segment replaces at least a portion of the heat lost due to axial expansion through the separating segment. The fluid then flows into a next inlet 430, and into a next separating segment 435. The mobile phase then flows through a next outlet 440 and through the outlet tubing 445.

Figure 5:
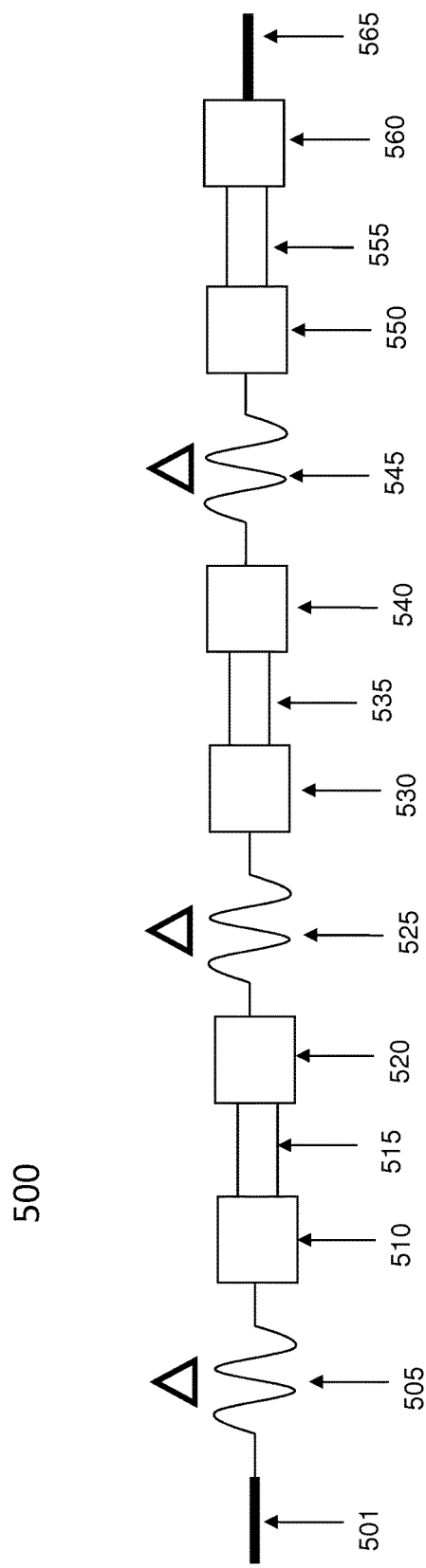
FIG. 5 shows yet another embodiment of the apparatus of the present technology.

FIG. 5 shows another embodiment of the segmented separation device 500 in accordance with the present technology. Device 500 features multiple iterations of the technique of flowing the sample stream through a separating segment followed by flowing the sample stream through a heating segment. In particular, FIG. 5 shows an embodiment including three non-contiguous separating segments, with a corresponding number of heating segments. The sample and mobile phase are introduced via the inlet tubing 501. The mobile phase then passes through an optional pre-heater 505. The pre-heater can be, but is not limited to, any of those described above. The sample then passes through an inlet 510 (e.g. an interconnecting tubing) and into a separating segment 515. The mobile phase then passes through an outlet 520 and through a heating segment 525. The heating segment replaces at least a portion of the heat lost due to axial expansion through the separating segment. The fluid then flows into a next inlet 530, and into a next separating segment 535. The mobile phase then flows through a next outlet 540 and through another heating segment 545. Heating segment 545 replaces at least a portion of the heat lost due to axial expansion through any of the previous separating segments. The sample then flows through another inlet 550, and through the separating segment 555. The sample exits through the outlet to the separating segment 560, and through a next outlet 565.

FIG. 5 shows an embodiment including three separating segments, a pre-heater, and two heating segments. In some embodiments, the number of heating segments can be between one and five. For example, the number of heating segments, not including pre-heater, can be two, three, or four. In embodiments, the number of heating segments included within a segmented separation device depends upon the number of separating segments. In some embodiments, the ratio of separating segments to heating segments is 1:2. In other embodiments, the ratio is 1:1. As shown in FIG. 5, in some preferred embodiments, the segments of the chromatographic system alternate between heating segments and separating segments in sequence.

In some embodiments of the technology, very short separating segments in combination with corresponding heaters will lead to minimal decreases in temperature, because the mobile phase will have only a short distance to travel, and thus expand, if the separating segment is short. Correspondingly, there would be less of a need for a heater after such a short segment because minimal heat would be lost. In some embodiments, use of a large number of short separating segments (e.g. much greater than 5 segments) could lead to band spreading because such an embodiment would also require a relatively high number of heating elements (e.g. much greater than 5 segments) as well as corresponding interconnecting tubing between the separating and heating segments, thereby increasing the overall dead volume of the system. Thus, in some embodiments, it is preferable to use a moderate number of separating segments (e.g. 2-5) and corresponding heating segments. In such preferred embodiments, the amount of interconnecting tubing is minimized, thus helping reduce bandspreading.

Figure 6:
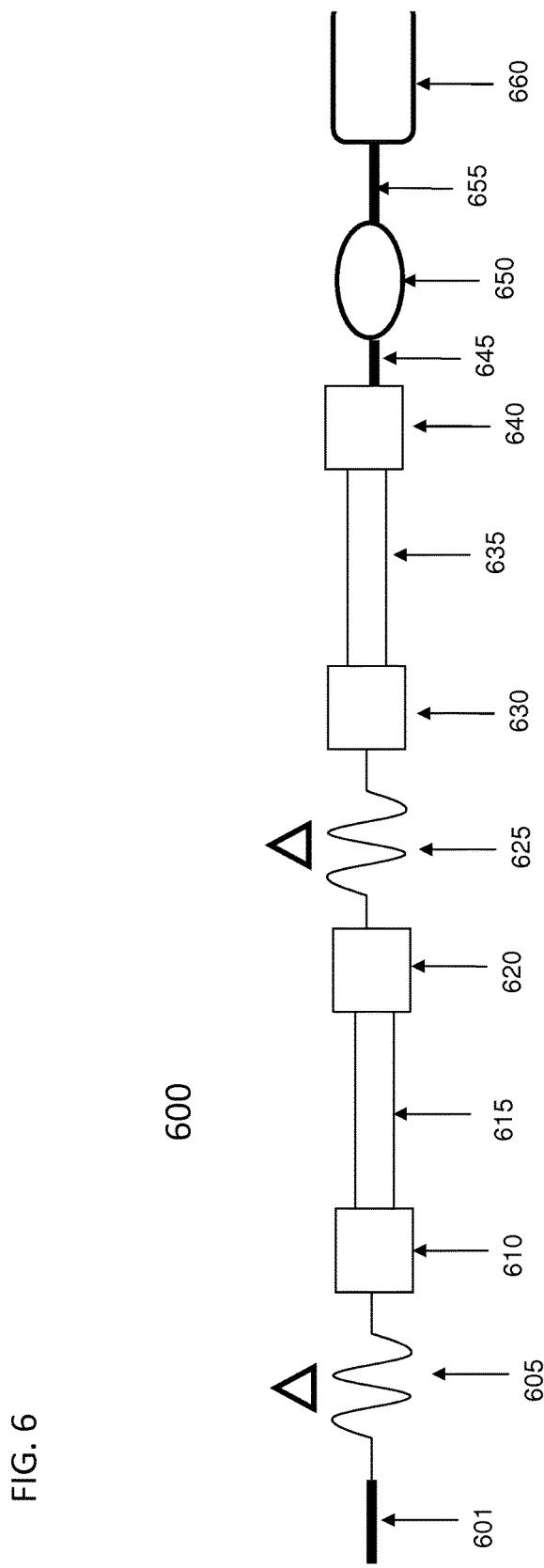
FIG. 6 shows still yet another embodiment of the apparatus of the present technology.

FIG. 6 shows another embodiment of a segmented separation device 600 in accordance with the present technology. Embodiment 600 features the use of an optional sample detector and sample collector. The sample and mobile phase are introduced via the inlet tubing 601. The mobile phase then passes through an optional pre-heater 605. The pre-heater can be, but is not limited to, any of those described above. The sample then passes through an inlet 610 and into the separating segment 615. The mobile phase then passes through an outlet 620 and through a heating segment 625. The heating segment replaces at least a portion of the heat lost due to axial expansion through the separating segment. The fluid then flows into a next inlet 630, and into the next separating segment 635. The mobile phase then flows through a next outlet 640 and through the outlet tubing 645. The sample can then be detected by a detector 650, and flow through the detector outlet 655 before being subsequently collected by a collector 660. While any type of detector can be used in embodiment 600, an exemplary device is a Waters UV/Vis detector such as the ACQUITY UPC$^2$ PDA detector. Correspondingly, while any type of sample collector can be used in embodiment 600, an exemplary device is the Waters WFCIII collector. Both of these instruments are available from Waters Technologies Corporation, Milford, Mass., USA.

Figure 7:
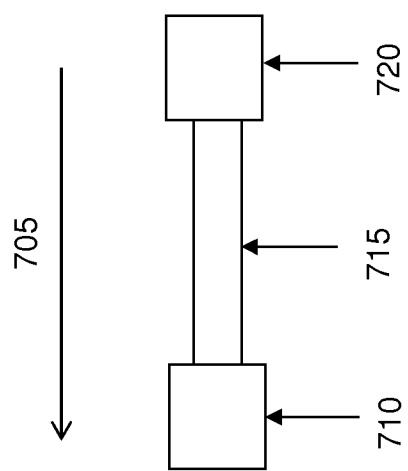
FIG. 7 shows an embodiment of the present technology in which heat is applied to a contiguous separating segment in an outlet-to-inlet direction

In addition to the above examples which focus on multiple separation segments which are divided by heating segments, other embodiments of the technology are possible. For instance, in some embodiments of the technology, a single separation segment or contiguous segments are used. Heat is applied directly to the separating segment (or segments) in an axial fashion, in an outlet-to-inlet direction. FIG. 7 shows a schematic 700 of an embodiment of the technology in which heat is applied to a single separating segment in an outlet-to inlet direction. As shown in scheme 700, a contiguous separating segment 715 is in fluid communication with an inlet 710 and an outlet 720. The sample and mobile phase are introduced through the inlet 710 and pass through the separating segment and exits through the outlet 720. Arrow 705 shows the direction of the axial application of heat. As shown, heat is applied axially in an outlet-to-inlet direction. The heat can be applied with a number of heaters, including any of the heaters described herein. The heat may also be applied to the outside of the single or contiguous separating segment.

In some embodiments, this type of heating allows the mobile phase to be heated precisely at the point where cooling due to axial expansion is most severe. For instance, as a mobile phase, including carbon dioxide at standard chromatography operating pressures and temperatures, travels through a column and expands in the axial direction, the cooling it experiences due to the axial expansion can be more pronounced towards the outlet of the chromatographic column compared with the inlet to the column. Therefore, in some embodiments heat is applied in an axial direction opposite to the direction of axial expansion of the mobile phase. Thus, more heat is applied at points in the column where cooling is more pronounced (e.g. towards the outlet of the column, or more specifically, towards the radial center of the outlet of the column) and less heat is applied at points in the column where the cooling is less pronounced (e.g. towards the inlet of the column).

Another advantage of heating a single separating segment in an axial fashion in an outlet-to-inlet direction is that in some embodiments it can help to reduce the cooling gradient experienced by the mobile phase. The mobile phase can experience a temperature gradient as it expands axially and, for instance, be cooler towards the column outlet than it is near the inlet. By establishing in some embodiments a counter-gradient of heat by the application of heat in an axial direction (outlet-to-inlet), the technology can ensure a more homogenous mobile phase from the column inlet to the column outlet. Yet another advantage is the minimization of dead volume.

A skilled artisan will appreciate that although the above descriptions offer some optional embodiments of the technology, there are many other configurations and embodiments of the technology that are possible. The above examples should not be construed in any way as limiting the number of conceivable embodiments or configurations of the present technology.

The technology described herein is applicable to chromatography instruments at both preparative and analytical scales. Various dimension and capacity designs can be adapted to fit to chromatography instruments based on processing capabilities. Overall improvements in chromatography can be achieved from all these designs.

Although various aspects of the disclosed methods and apparatus have been shown and described, modifications can occur to those skilled in the art upon reading the specification. The present application includes such modifications. For example, while the separations described herein have been exemplified as SFC and/or $CO_2$-based chromatography separations, it is understood that the methods and apparatuses are applicable in 1D and 2D separations as well as a mix of SFC and LC separations. For example, in one or more embodiments, the technology can be directed to a supercritical fluid chromatography (SFC) separation followed by a hydrophilic interaction liquid chromatography (HILIC) separation. Alternatively, in some embodiments, the technology can be directed to a hydrophilic interaction liquid chromatography (HILIC) separation followed by a supercritical fluid chromatography (SFC) separation. In some embodiments, the technology can be directed to a reverse phase liquid chromatography (LC) separation followed by a supercritical fluid chromatography (SFC) separation. In one or more embodiments, the technology can be directed to an enhanced fluidity reverse-phase separation followed by a supercritical fluid chromatography (SFC) separation. In some embodiments, the technology can be directed to a size exclusion liquid chromatography (LC) separation followed by a supercritical fluid chromatography (SFC) separation. In some embodiments, the technology can be directed to a supercritical fluid chromatography (SFC) separation followed by a size exclusion liquid chromatography (LC) separation. In some embodiments, the technology can be directed to a supercritical fluid chromatography (SFC) separation followed by an ion exchange liquid chromatography separation.

In addition to the above description, the following non-limiting examples are provided for illustrative purposes.

Example 1

A supercritical fluid chromatography system was provided. The chromatography system comprised a sample injection port in fluid communication with a preheater, a first separating segment, a heating segment, a second separating segment and a detector. The separating segments were each 3.0×50 mm columns including bridged ethylene hybrid 5 μm particles as the stationary phase. The heating segment was a standard preheater disposed between the two separating segments. The mobile phase comprised 100% $CO_2$, with an internal column temperature of 50° C., and a back pressure of 1100 psi. The initial mobile phase flow rate was 2.85 mL/min.

Figure 8A:
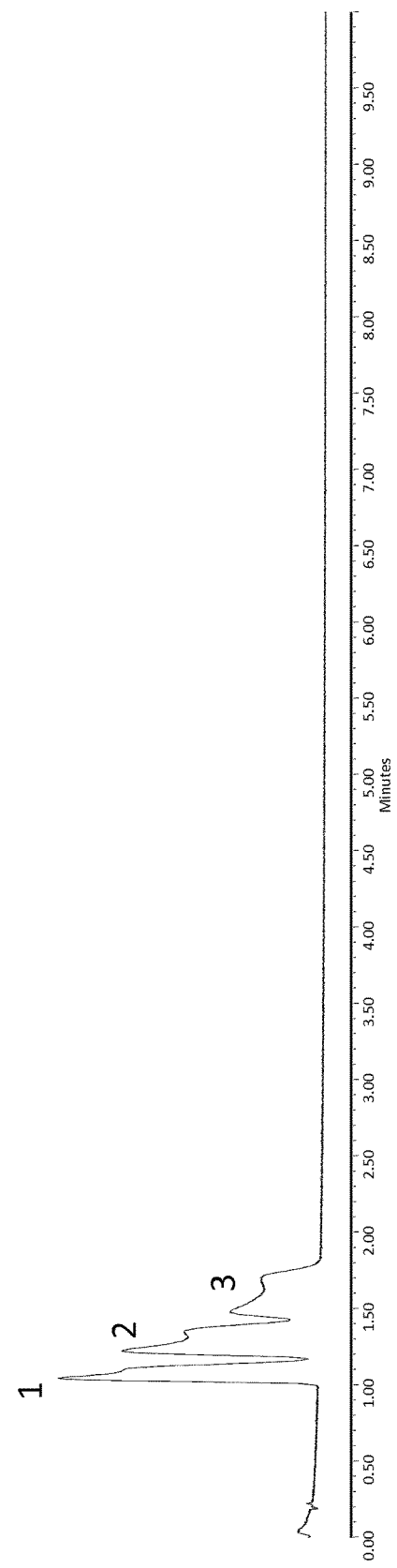
FIG. 8A shows a chromatogram of an SFC separation using a disabled heating segment to mimic standard SFC conditions (e.g. no heating of mobile phase between separating segments).

In the first run, the first preheater was active and the heating segment disposed between the two separating segments was inactive to mimic the conditions of utilizing a single separating segment (e.g. a single chromatography column) without heating between the segments. A sample comprising butylphenone, octylphenone and dodecanophenone (1 μL; 0.005 M in heptane) was injected. As seen in FIG. 8A, the peak shape of all three peaks (butylphenone, peak 1; octylphenone, peak 2; and dodecanophenone, peak 3) were distorted due to the heterogeneity of the mobile phase brought about as a result of axial expansion of mobile phase down the length of the separating segments. The peaks were difficult to resolve, leading to an incomplete separation.

Figure 8B:
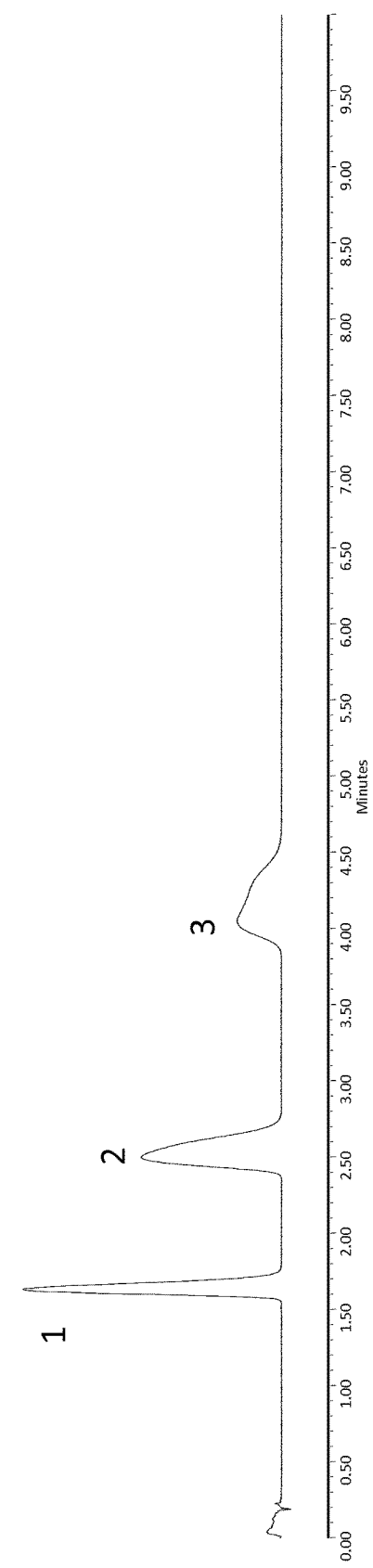
FIG. 8B shows a chromatogram of an SFC separation using an active heating segment between two separating segments.

In the second run, the first preheater was active and the second heating segment disposed between the two separating segments was also active to heat the mobile phase after passing through the first separating segment. The same sample comprising butylphenone, octylphenone and dodecanophenone (1 μL; 0.005 M in heptane) was injected. As seen in FIG. 8B, the peak shapes are less distorted than they were in FIG. 8A, and the separation between peaks is better. This result suggests that the second heating element is responsible for replacing at least a portion of the heat lost due to axial expansion of the mobile phase, and thus ensuring a more homogenous mobile phase to give a more effective separation of the sample.

Figure 8C:
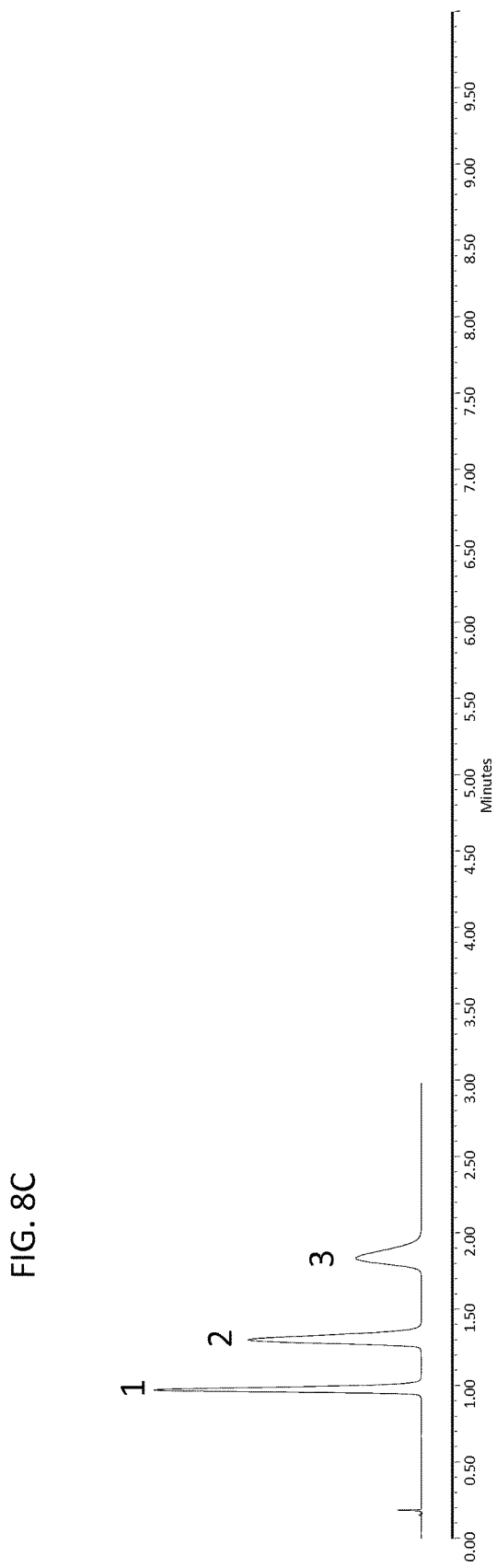
FIG. 8C shows a chromatogram of optimized SFC conditions using an active heating segment between two separating segments.

In the third run, the first preheater was active and the second heating segment disposed between the two separating segments was also active to heat the mobile phase after passing through the first separating segment. The mobile phase flow rate was also increased from 2.85 mL/min to 3.4 mL/min. Once again, the same sample comprising butylphenone, octylphenone and dodecanophenone (1 μL; 0.005 M in heptane) was injected. As seen in FIG. 8C, the peak shapes are less distorted and narrower than they are in FIGS. 8A and 8B, and the separation between peaks is better. This result suggests that the second heating element is responsible for replacing at least a portion of the heat lost due to axial expansion, and thus ensuring a more homogenous mobile phase to give a more effective separation of the sample.

The above results show a drastic reduction in peak width and improvement in shape from run 1 to run 3, which in turn improves the analysis and results of the chromatograms. For example, in embodiments of the present technology, USP efficiencies (calculated from the 50% width) from run 1 to run 2 were improved by 348%, 384%, and 1734% for peaks 1, 2, and 3, respectively. Additionally, USP efficiencies improved from run 2 to run 3 by 227%, 377%, and 540% for peaks 1, 2 and 3, respectively.

Example 2

A supercritical fluid chromatography system will be provided, in which carbon dioxide ($CO_2$) is allowed to flow through a flow meter and a $CO_2$ pump designed to pump supercritical or near supercritical $CO_2$. A second pump delivers methanol to serve as a modifier fluid. The supercritical $CO_2$ and methanol are combined to form a single mobile phase. The mobile phase comprises 90% $CO_2$ and 10% methanol at a flow rate of 3.4 mL/min, at 50° C., with about 1100 psi backpressure maintained with a backpressure regulator. An analyte (e.g. a mixture of 8 mg each butylphenone, octylphenone, and dodecanophenone) will be injected (1 μL, 0.005 M in heptane) into the combined single mobile phase, which is then flowed through a pre-heater. The pre-heater is a clip on pre-heater held statically at 473 K, and has a length of 2 cm and an internal diameter of 5 mm. The mobile phase is then flowed through a first separating segment. The first separating segment is cylindrical and has a length of 5 cm and an internal diameter of 4.6 mm. The first separating segment is packed with round silica particles. The mobile phase will then be flowed through a first active heater. The first heater is a traditional oven, and the temperature of the first heater is controlled by a feedback loop connected to a thermometer located near the outlet of the first separating segment. The first heater and the feedback loop work together to ensure that the temperature of the mobile phase exiting the first heater is about 473 K. The first heater has a length of 4 cm and an internal diameter of 4 mm. The mobile phase then flows through a second separating segment. The second separating segment is cylindrical and has a length of 5 cm and an internal diameter of 4.6 mm. The second separating segment is also packed with round silica particles. The mobile phase then passes through a second active heater. The second heater is an isothermal oven. The second heater is held at a temperature of about 500 K. The second heater has a length of 6 cm and an internal diameter of 5.5 cm. The mobile phase will then be flowed through a detector to detect the sample of interest.

Example 3

A supercritical fluid chromatography system will be provided in which two separating segments are connected in series with a preheater and an active heater disposed between the separating segments. A pump will be used to pump supercritical or near supercritical $CO_2$ through the system, as well as modifier solvents and additives. The mobile phase comprises $CO_2$ (90%) as well as methanol, a modifier (9%) and acetic acid, an additive (1%). The separating segments are wrapped in aluminum foil to enhance the radial thermal gradients produced by the enthalpic expansion and cooling of the mobile phase. An analyte (e.g. a mixture of 10 mg each butylphenone, octylphenone, and dodecanophenone) will be injected (1 µL, 0.005 M in heptane) into the mobile phase at a flow rate of 2.85 mL/min, at 50° C., with about 1200 psi backpressure (maintained with a backpressure regulator), with both of the heaters (e.g. the pre heater and the active heater) active. The mobile phase will first be flowed through a pre heater held at about 500 K. The pre heater is a microwave type heater, with a length of 4.5 cm and an internal diameter of 4 mm. The mobile phase is then flowed through a first separating segment. The stationary phase of the first separating segment is a polymeric fully porous monolith. The mobile phase is then flowed through an active heater. The active heater is a traditional oven with a length of 6 cm and an internal diameter of 5 mm, and is coupled to a feedback loop to ensure that a mobile phase temperature of about 525 K is maintained. The mobile phase is then flowed through a second separating segment. The second separating segment has an internal diameter of 5.5 mm and a length of 5 cm. The stationary phase within the second separating segment is a polymeric fully porous monolith. After passing through the second separating segment, the mobile phase will be passed through a UV-Vis detector to measure the separation and collected in fractions.

What is claimed is:

1. A method for separating a sample in a compressible fluid chromatography device defining a flow path, the device comprises a plurality of segments for separating the sample and/or heating at least a portion of the flow path, the method comprising:
introducing the sample into the compressible fluid chromatography device;
separating the sample along at least two non-contiguous segments of the compressible fluid chromatography device along the flow path, wherein the said non-contiguous segments are separated by a heating segment; and
heating one or more of the plurality of segments of the compressible fluid chromatography device to reduce heat lost due to expansion of the compressible fluid along the flow path.

2. The method of claim 1, further comprising collecting fractions of the sample after separation.

3. The method of claim 1, wherein multiple different types of separating segments are used.

4. The method of claim 1, wherein the separating segments used are of the same type.

5. The method of claim 1, further comprising pre-heating the sample before separation with a pre-heater.

6. The method of claim 1, wherein the heating segment has the characteristics of a pre-heater.

7. The method of claim 1, wherein the compressible fluid is carbon dioxide.

8. The method of claim 7, wherein the carbon dioxide is at supercritical conditions within at least a portion of the at least two non-contiguous segments during separation of the sample.

9. The method of claim 1, wherein the compressible fluid is a chlorofluorocarbon.

10. The method of claim 9 wherein the compressible fluid is Freon.

11. The method of claim 1 wherein the compressible fluid is $N_2O$.

12. The method of claim 1 wherein the compressible fluid is $SF_6$.

13. A method for separating a sample in a carbon dioxide-based chromatography device defining a flow path, the method comprising:
providing a carbon dioxide-based chromatography device including a plurality of segments for separating the sample and/or heating at least a portion of the flow path;
introducing the sample into the chromatography device;
separating the sample along at least two non-contiguous segments of the flow path of the mobile phase through the device; and
heating at least one of the plurality of segments disposed between the two non-contiguous segments of the flow path of the chromatography device to reduce the heat lost due to expansion of the carbon dioxide along the fluid path.

14. The method of claim 13, further comprising collecting fractions of the sample after separation.

15. The method of claim 13, wherein multiple different types of separating segments are used.

16. The method of claim 13, wherein the separating segments used are of the same type.

17. The method of claim 13, further comprising pre-heating the sample before separation with a pre-heater.

18. The method of claim 13, wherein the heating segment has the characteristics of a pre-heater.

19. The method of claim 13, wherein the carbon dioxide mobile phase is at or near supercritical conditions within at least a portion of the at least two non-contiguous segments during separation of the sample.

* * * * *